United States Patent [19]

Martin

[11] 4,225,720

[45] Sep. 30, 1980

[54] PURIFICATION OF AT-125

[75] Inventor: David G. Martin, Kalamazoo, Mich.

[73] Assignee: The Upjohn Company, Kalamazoo, Mich.

[21] Appl. No.: 634

[22] Filed: Jan. 2, 1979

Related U.S. Application Data

[60] Division of Ser. No. 918,569, Jun. 23, 1978, which is a continuation-in-part of Ser. No. 906,028, May 15, 1978, abandoned.

[51] Int. Cl.$^3$ .................... C07D 413/12; A61K 31/42
[52] U.S. Cl. ..................................... 548/240; 424/272
[58] Field of Search ..................... 260/307 F; 548/240

[56] References Cited

U.S. PATENT DOCUMENTS

| | | | |
|---|---|---|---|
| 3,856,807 | 12/1974 | Hanka et al. | 260/307 F |
| 3,944,562 | 3/1976 | Martin et al. | 260/307 F |

Primary Examiner—Mary C. Lee
Attorney, Agent, or Firm—Sidney B. Williams, Jr.

[57] ABSTRACT

Process for the purification of L-($\alpha$S,5S)-$\alpha$-amino-3-chloro-4,5-dihydro-5-isoxazoleacetic acid (AT-125). Also provided are AT-125 analogs prepared in the process.

4 Claims, No Drawings

PURIFICATION OF AT-125

The invention described herein was made in the course of, or under, Contracts No. 1-CM-43753 and No. 1-CM-77100 with the National Cancer Institute, National Institute of Health, Bethesda, Md. 20014.

CROSS REFERENCE TO RELATED APPLICATION

This is a division of application Ser. No. 918,569, filed June 23, 1978, which is a continuation-in-part of Ser. No. 906,028, filed May, 15, 1978, now abandoned.

BACKGROUND OF THE INVENTION (1) Field of the Invention

The invention concerns a novel process for purifying large batches of impure AT-125. The process involves converting impure AT-125 to a derivative from which pure AT-125 can be generated. The invention also includes novel analogs prepared and used in the process. Some of the analogs also have antitumor and antimicrobial activity.

(2) Description of the prior art

AT-125 which can be represented by structure of formula I

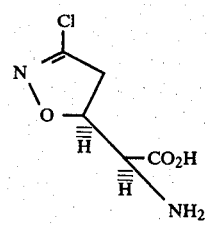

and a microbiological process for producing it are disclosed and claimed in U.S. Pat. Nos. 3,856,807 and 3,878,047, respectively. These patents also disclose the antitumor and antimicrobial activities of AT-125.

The concept of separating refractory mixtures or purifying a contaminated material via a derivative from which the desired compound(s) can be regenerated is not novel. As an example, biotin antimetabolites, α-methylbiotin, α-dehydrobiotin, and α-methyldethiobiotin were separated as their phenacyl esters [Martin et al., Tetrahedron Letters pp. 3791–3794 (1971)].

Background information on preparation and removal of phthalimido, p-nitrobenzyl esters of carbobenzyloxy, and carbotertbutyloxy derivatives of amino acids is found in R. A. Boissonnas chapter, "Selectively Removable Amino Protective Groups used in the Synthesis of Peptides," In: Advances in Organic Chemistry, 3:159–190 (1963), editors Raphael et al., Interscience Publishers.

Background information on the 9-fluorenylmethoxy carbonyl amino protecting group is found in J. Org. Chem. 37:3404–3409 (1972) (Carpino et al.).

Information on the t-butoxy carbonyl amino protecting group described is ALDRICH'S technical information on BOC-ON, September, 1976.

Chromatographic separation (conventional and high performance liquid chromatography (HPLC)) of AT-125 mixtures have been attempted and although chromatographic separation is feasible, solubility limitations make large-scale application difficult and inconvenient.

However, the combination of very low solubility in organic solvents and similar chromatographic mobilities of components in the AT-125 mixture prepared as described in U.S. Pat. Nos. 3,856,807 and 3,878,047 has made final purification of AT-125 extremely difficult on a large scale. Recrystallization from methanol accomplished little; an improved crystallization procedure from aqueous secondary butanol removed some contaminants but left others. Countercurrent distribution afforded partial resolution and some pure material but the process suffered from solubility limitations and emulsions and offered little hope for large-scale application.

SUMMARY OF THE INVENTION

The novel process of this invention can readily and conveniently be utilized to purify relatively large batches of impure AT-125.

The process may be represented schematically as follows:

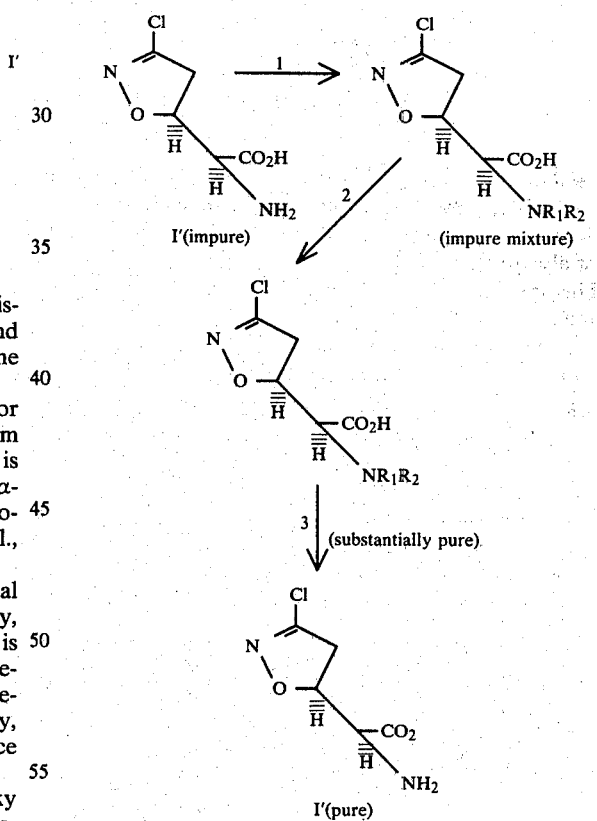

wherein $R_1$ and $R_2$ are selected from the group consisting of hydrogen, $$-\overset{O}{\underset{\|}{C}}OR_3,$$

or when taken together with the nitrogen atom form the group

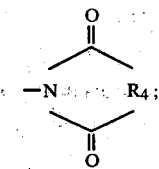

wherein $R_3$ is alkyl of from 1 to 3 carbon atoms, inclusive, halogenated alkyl of from 1 to 5 carbon atoms, inclusive, and 1 to 3 halogen atoms, inclusive aryl of from 6 to 20 carbon atoms, inclusive, aralkyl and substituted aralkyl of from 7 to 20 carbon atoms, inclusive, $R_4$ is selected from the group consisting of (a)

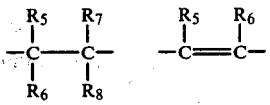

where $R_5$, $R_6$, $R_7$ and $R_8$ are selected from the group consisting of hydrogen and alkyl of from 1 to 5 carbon atoms, inclusive, (b)

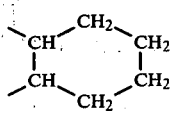

(c) orthointerphenylene and (d) substituted orthointerphenylene with the proviso that other than when $R_1$ and $R_2$ form a ring with the nitrogen atom, one of $R_1$ or $R_2$ must always be hydrogen.

This invention also includes compounds having the formula

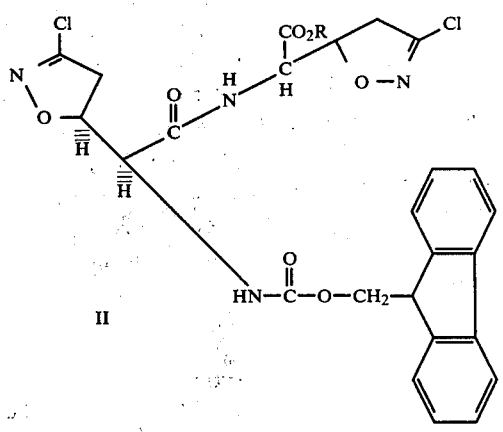

wherein R is selected from the group consisting of hydrogen and alkyl of from 1 to 8 carbon atoms; and $R_1$ and $R_2$ are different and are selected from the group consisting of hydrogen

or when taken together with the nitrogen atom form the group

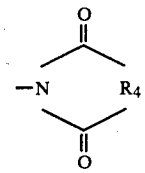

wherein $R_3$ is alkyl of from 1 to 8 carbon atoms, inclusive, and $R_4$ is selected from the group consisting of (a)

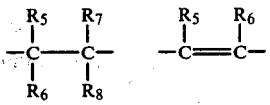

where $R_5$, $R_6$, $R_7$ and $R_8$ are selected from the group consisting of hydrogen and alkyl of from 1 to 5 carbon atoms, inclusive, (b)

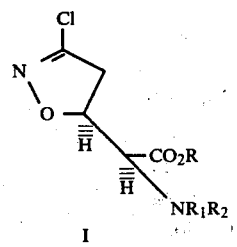

(c) orthointerphenylene, and (d) substituted orthointerphenylene with the proviso that other than when $R_1$ and $R_2$ form a ring with the nitrogen atom one of $R_1$ and $R_2$ must always be hydrogen.

In the foregoing designation of variables, "Loweralkyl" means methyl, ethyl, propyl, butyl, pentyl, hexyl, heptyl, octyl and the isomeric forms thereof.

Halogenated alkyl of from 1 to 5 carbon atoms, inclusive, and 1 to 3 carbon atoms, inclusive, means methyl, ethyl, propyl, butyl, pentyl and isomeric forms thereof substituted by 1 to 3 bromine, fluorine, chlorine or iodine atoms.

"Aralkyl" means benzyl, phenethyl, phenpropyl, phenbutyl, phenpentyl, diphenylmethyl, three diphenyloctyl and isomeric forms thereof and fluorenylmethyl.

"Substituted aralkyl" means aralkyl in which the phenyl ring containing substituents selected from the group consisting of alkoxy, alkyl halogen and nitro. For example, p-methoxybenzyl, m-methoxybenzyl, p-nitrobenzyl, p-chlorobenzyl.

"Substituted orthointerphenylene" means loweralkyl, lower-alkoxy, halogen, nitro, and cyano substituted orthointerphenylene. There can be combinations of substituents such as 4-propyl-2-methyl-, 2-chloro-4-methyl-, 3,4-diethoxy-3-cyano-4-ethoxyphenoxy and the like. The substituted phenoxy is limited to a total of 10 carbon atoms.

"Halogen" means bromine, chlorine, fluorine and iodine.

DETAILED DESCRIPTION OF THE INVENTION

The novel process of this invention involves converting AT-125 to a derivative, separating the derivative from the reaction mixture and then regenerating AT-125 from the derivative. Required of a derivative process include (1) formation of the derivative (2) facile purification of the derivative (3) essentially quantitative regeneration of the AT-125 and (4) applicability to reasonably large-scale operation.

The aralkoxycarbonyl, substituted aralkoxycarbonyl, and phthalimido derivatives are usable in the process, but the alkoxycarbonyl derivatives, in particular t-butyloxycarbonyl yield the best results and therefore are the preferred derivatives to be used.

Step 1 involves reacting a mixture of AT-125 with a blocking agent in the presence of a solvent and an acid acceptor to produce a mixture containing AT-125 derivative and contaminants. The reaction is conducted at a temperature of 0° to 100° C. and for a period of 5 minutes to 72 hours. The molar ratio of blocking agent to AT-125 present in the mixture is 1 to 2. Solvents that can be used include tetrahydrofuran, dimethyl formamide, acetonitrile, alcohols, dioxane, aqueous mixtures thereof and water. The preferred solvent when t-butyloxycarbonyl is the blocking group is aqueous dioxane Acid acceptors that can be used include triethyl amine, pyridine, sodium hydroxide, sodium bicarbonate and other inorganic bases. The preferred acid acceptor is triethylamine.

The blocking agents that can be used in this step are readily available from commercial sources or can be made by methods well known in the art For example, 2-(tert-butoxycarbonyloxyimino)-2-phenylacetonitrile is readily available under the trade name of BOC-ON.

Step 2 involves separating AT-125 derivative from the mixture formed in step 1. Solvent extraction at the appropriate pH followed by chromatography on adsorbents such as silica gel, alumina, or florisil or ion exchange resins, or partition chromatography, or Craig Counter current distribution or other methods known in the art.

The preferred method is to chromatograph the mixture on silica gel using methylene chloride:isopropanol:acetic acid as the eluant. The ratio of methylene chloride:isopropanol:to acetic acid in the eluant can range from 100:1:1 to 100:10:1.

Step 3 involves removal of the blocking group under appropriate conditions such as with acids, e.g. formic acid, hydrochloric acid, and the like, for acid-sensitive groups, e.g. t-butyloxycarbonyl or bases, e.g. ammonia lower aliphatic amine, or hydrazine for base-sensitive groups, e.g. fluorenylmethyloxycarbonyl, phthalimide, or hydrogenolytically for benzylic protecting groups. When $R_1$ is t-butyloxycarbonyl and $R_2$ is hydrogen step 3 involves reacting the purified AT-125 derivative separated in step 2 with an acid in the presence of a solvent such as ethyl acetate, acetonitrile, nitromethane and acetic acid to form an acid addition salt of AT-125. This reaction is conducted at a temperature of from about 0° to 50° for a period of about 5 minutes to 8 hours. Acids that can be used include hydrochloric acid, hydrobromic acid, hydroiodic acid, sulfuric acid, phosphoric acid, formic acid, trichloroacetic acid and the like. The preferred acid when t-butyloxycarbonyl is the blocking group is hydrochloric acid.

The next step when $R_1$ is t-butyloxycarbonyl involves neutralizing the acid addition salt formed and then crystallizing the AT-125 from aqueous alcohol to yield analytically pure AT-125. This step is conducted at a temperature of between 0° and 40° for a period of 4 hours to 72 hours and at a pH of from 4.5 to 6.5. The preferred temperature range is between 0° and 30° C. Alcohols that can be used to make up the aqueous alcoholic solution include 2-butanol, methanol, isopropanol, ethanol and n-butanol. The preferred alcohol is 2-butanol.

Compounds of formula II have shown antitumor activity superior to AT-125 and its other derivatives.

The compounds of this invention which can form salts, do so to give alkali metal salts, alkaline earth metal salts and amine salts. Metal salts can be prepared by dissolving them in water, and adding a dilute metal base until the pH of the solution is 7 to 8. Metal salts include the sodium, potassium and calcium salts. Amine salts, including those with organic bases such as primary, secondary, and tertiary, mono-, di-, and polyamines can also be formed using the above-described or other commonly employed procedures. Further, ammonium salts can be made, by well-known procedures. Other salts are obtained with therapeutically effective bases which impart additional therapeutic effects thereto. Such bases are, for example, the purine bases such as theophyllin, theobromin, caffein, or derivatives of such purine bases; antihistaminic bases which are capable of forming salts with weak acids; pyridine compounds such as nicotinic acid amide, isonicotinic acid hydrazide and the like; phenylalkylamines such as adrenalin, ephedrin, and the like; choline, and others. Base salts of the compounds can be used for the same biological purposes as the parent compound.

The compounds of formula II are also effective for treating bacterial infections and tumors in mammals, including humans.

The compositions of the present invention are presented for administration to humans and animals in unit dosage forms, such as tablets, capsules, pills, powders, granules, suppositories, sterile parenteral solutions or suspensions, eye drops, oral solutions or suspensions, and water-in-oil emulsions containing suitable quantities of the compound of formulas I and II.

E or oral administration, either solid or fluid unit dosage forms can be prepared. For preparing solid compositions such as tablets, the compounds of formula I and II are mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The term "unit dosage form", as used in the specification, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampoules, vials, aerosols with metered discharges, segregated multiples of any of the foregoing, and other forms as herein described.

The dosage of the compound for treatment depends on many factors that are well known to those skilled in the art. They include for example, the route of administration and the potency of the particular compound. A dosage schedule for humans of from about 100 mg to about 5 g of compound in a single dose, administered parenterally or in the compositions of this invention, are effective for treating tumors and bacterial infections, preferably, 100 mg to 2 g.

The following described preparations and examples are indicative of the scope of this invention and are not to be construed as limitative.

Preparation 1:
3-Chloro-α-[[(1,1-dimethylethoxy)carbonyl]amino]-4,5-dihydro-5-isoxazoleacetic acid

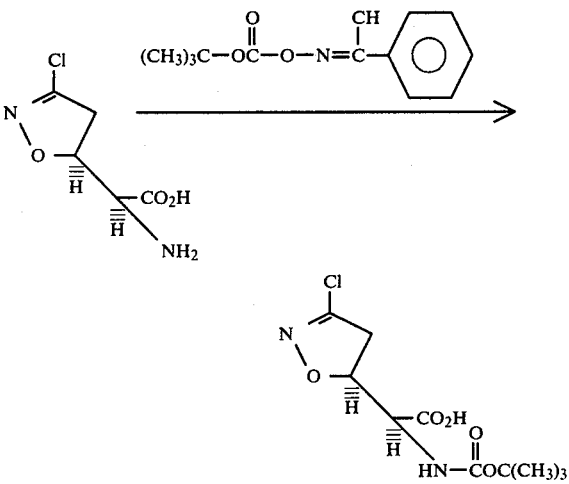

To 1.78 gm (8 mmoles) of 80% pure L-(α5,5S)-α-amino-3-chloro-isoxazoline-5-acetic acid stirred in 20 ml deionized water, 20 ml good quality dioxane and 2.t ml triethylamine is added 2.80 gm of [2-(tert-butyloxycarbonyloxyimino)-2-phenylacetonitrile] (Aldrich) and the mixture is stirred at room temperature for 16 hours. The dark solution is diluted to 350 ml with deionized water and filtered through a small celite pad. The pad is washed with a total of 50 ml of additional water and the combined filtrate cooled and brought from pH 7.8 to 3.1 by the addition of 42 ml of 10% aqueous citric acid. The acidified mixture is then extracted with three 300 ml portions of ethylacetate: each is washed with two 50 ml portions of water to remove citric acid and evaporated to dryness affording 4.9 gm, 0.1 gm, and 0.1 gm in the successive extracts. The extracted residues are dissolved in a small volume of methylene chloride and chromatographed on 260 ml of silica gel with methylene chloride:isopropanol:acetic acid (100:3:1). Fractions of 50 ml are collected; 5 μl of each fraction are spotted on a 13 mm disc, wet with a drop of 1 N ammonium hydroxide, dried briefly and spotted on a tray of B. subtilis synthetic 902. The [2-(tert-butyloxycarbonyloxyimino)-2-phenylacetonitrile] derivative is eluted in fractions 12-21; these fractions afford zones of 45, 55, 52, 49, 46, 43, 41, 39, 35, and 32 mm. Estimates of the product present in each fraction are made from these zone sizes by comparison with a standard curve.

Evaporation of fractions 12-21 leaves 2.56 gm of 3-chloro-α-[[(1,1-dimethylethoxy)carbonyl]amino]-4,5-dihydro-5-isoxazoleacetic acid as a colorless oily gum.

Preparation 2:
Phthalyl-(αS,5S)-2-amino-3-chloro-4,5-dihydro-5-isoxazoleacetic acid

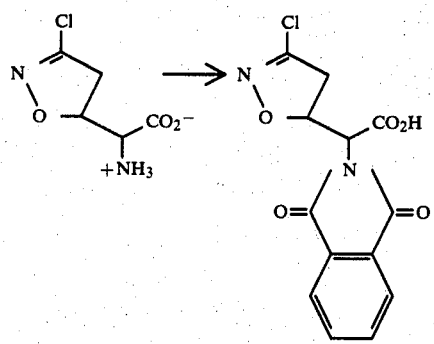

To 1.78 g of impure AT-125 (approximately 80% AT-125 present by *B. subtilis* synthesis 902 assay) in 212 ml cold water is added 2.30 g N carbethoxy phthalimide (Frinton Laboratories, recrystallized m.p. 89°) and 1.06 g of sodium carbonate and the mixture is blended in a Waring Blender for 40 minutes. The temperature rises from 5° C. to 36° C. The clear solution is concentrated under reduced pressure to 30 ml after adjusting the pH from 8 to 7. Acidification of the concentrate to pH 2.8 with aqueous hydrogen chloride causes the separation of a brown oil which is extracted with two 200 ml portion of ethyl acetate. The extracts are washed with brine and dried over magnesium sulphate, affording 3.21 g of foamy gum. This gum is chromatographed on 640 ml of silica gel (E. Merck Darmstaadt) eluting with methylene chloride:isopropyl alcohol:acetic acid (100:3:1 is employed) and collecting 500-ml fractions Column fractions are monitored by UV visualized TLC. Fractions 3 and 4, containing 1.179 g of viscous oil, are chromatographically homogeneous phthalimido derivative. Crystallization afforded 936 mg of crystalline product, m.p. 171°–173° C. Two recrystallizations of this product from acetone-toluene afforded the analytically pure phthalyl(αS,5S)-α-amino-3-chloro-4,5-dihydro-5-isoxazoleacetic acid, m.p. 176°–177° C.

Analysis Calc'd for $C_{13}H_9ClN_2O_5$: C, 50.58; H, 2.94; N, 9.08; Cl, 11.49. Found: C, 50.88; H, 2.91; N, 9.14; Cl, 11.52.

NMR and IR spectra are consistent with the structure (PAC No. 76 15776). The U.V. spectrum in ethanol showed end absorption with a shoulder at 210 nm ($\epsilon$ 40,700) and $\gamma_{max}$ 234 nm ($\epsilon$ 1.950).

Preparation 3:
3-Chloro-4,5-dihydro-α-[[[(4-nitrophenyl)methoxy]carbonyl]amino]-5-isoxazoleacetic acid

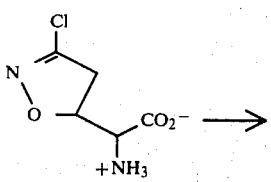

-continued

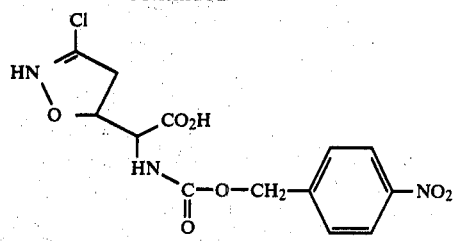

A mixture of 1.65 g impure AT-125 (85% pure by bioassay), 4.72 g potassium bicarbonate, and 3.00 g of p-nitrobenzylchloroformate is stirred in 46 ml of water at room temperature for 3½ hours. The mixture is diluted with water and extracted with 2 portions of ethyl acetate to remove components derived solely from the chloroformate; the aqueous layer is acidified to pH 2 with aqueous hydrogen chloride and extracted with 2 portions of ethyl acetate. The extracts are washed with water and evaporated affording 2.50 g of oily crude material which is chromatographed on 520 ml of silica gel with methylene chloride, isopropanol, and acetic acid (100:3:1). Fractions of 50 ml are collected. Fractions 27-64 contain 2.50 g of chromatographically homogeneous product as a viscous oil. Crystallization from methylene chloride affords 1.73 g of crystalline 3-chloro-4,5-dihydro-α-[[[(4-nitrophenyl)methoxy]carbonyl]amino]-5-isoxazoleacetic acid, m.p. 141.5°–142°. A sample recrystallized from methylene chloride melts at 143°–144° C.

Analysis Calc'd for $C_{13}H_{12}ClN_3O_7$: C, 43.65; H, 3.38; Cl, 9.91; N, 11.75. Found: C, 43.83; H, 3.47; Cl, 9.94; N, 11.79.

Preparation 4:
3-Chloro-α-[[(9H-fluoren-9-ylmethoxy)carbonyl]amino]-4,5-dihydro-5-isoxazoleacetic acid and 3-chloro-α-[[(3-chloro-4,5-dihydro-5-isoxazolyl)[[9H-fluoren-9-ylmethoxy)carbonyl]amino]acetyl]amino]-4,5-dihydro-5-isoxazoleacetic acid

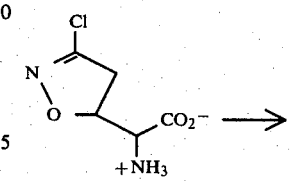

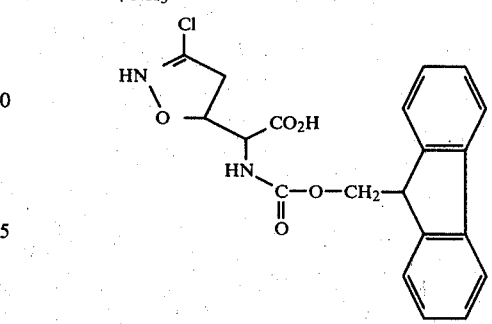

-continued

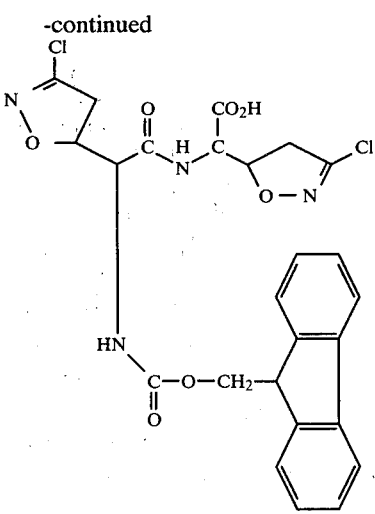

A mixture of AT-125 (178 mg; 1 mmole), 9 fluorenyl-methylchloroformate (285 mg, 1.1 mmole), and potassium bicarbonate (370 mg; 3.7 mmole) in 5 ml of water was stirred for 20 hours at room temperature. The gelatinous mixture is acidified to pH 2 with hydrochloric acid, evaporated to dryness under reduced pressure, and extracted with acetone. The acetone extracts are adsorbed onto silica gel and chromatographed on 40 g of silica gel with methylene chloride:isopropanol:acetic acid (100:3:1). Fractions of 20 ml are collected and monitored by TLC (U.S. visualization). The first 8 fractions contain components derived from the chloroformate reagent only including 9-fluorenylmethyl alcohol. Fractions 11–17 contain 206 mg of chromatographically homogeneous 3-chloro-α-[[(9H-fluoren-9-yl-methoxy)-carbonyl]amino]-4,5-dihydro-5-isoxazoleacetic acid, and fractions 21-50 contain 132 mg of chromatographically homogeneous 3-chloro-α-[[(3-chloro-4,5-dihydro-5-isoxazolyl)[[(9H-fluoren-9-ylmethoxy)carbonyl]amino]acetyl]amino]-4,5-dihydro-5-isoxazoleacetic acid. Crystallization of fractions 11–17 from aqueous methanol and recrystallization from acetone-cyclohexane yields 3-chloro-α-[[(9H-fluoren-9-ylmethoxy)carbonyl]amino]-4,5-dihydro-5-isoxazoleacetic acid m.p. 175°–176°.

Analysis Calc'd for $C_{20}H_{17}ClN_2O_5$: C, 59.93; H, 4.28; Cl, 8.85; N, 6.99. Found: C, 60.03; H, 4.26; Cl, 8.94; N, 6.86.

Its U.V., NMR and IR spectra are consistent with its structure.

The 3-chloro-α-[[(3-chloro-4,5-dihydro-5-isoxazolyl)-[[(9H-fluoren-9-ylmethoxy)carbonyl]amino]acetyl]amino]-4,5-dihydro-5-isoxazoleacetic acid fraction gives a NMR spectrum that is consistent with its structure. After precipitation from acetone solutions with cyclohexane, the resulting solid shows the following analysis Analysis Calc'd for $C_{25}H_{22}ClN_4O_7$: C, 53.49; H, 3.95; Cl, 12.63; N, 9.98. Found: C, 53.46; H, 4.30; Cl, 12.25; N, 9.79.

Its U.V. and IR spectra are reasonable for the structure.

Preparation 4a

Both 3-chloro-α-[[(9H-fluoren-9-ylmethoxy)carbonyl]-amino]-4,5-dihydro-5-isoxazoleacetic acid and 3-chloro-α-[[(3-chloro-4,5-dihydro-5-isoxazolyl)[[(9H-fluoren-9-yl-methoxy)carbonyl]amino]acetyl]amino]-4,5-dihydro-5-isoxazolacetic acid can be more conveniently isolated from the reaction medium as a crude mixture by extraction of the acidified reaction mixture with ethyl acetate. Extraction of the basic mixture before acidification can be used to separate products derived solely from the chloroformate but emulsions caused some problems.

Preparation 5:
3-Chloro-α-[[(3-chloro-4,5-dihydro-5-isoxazolyl)[[(9H-fluoren-9-ylmethoxy)carbonyl]amino]acetyl]amino]-4,5-dihydro-5-isoxazoleacetic acid

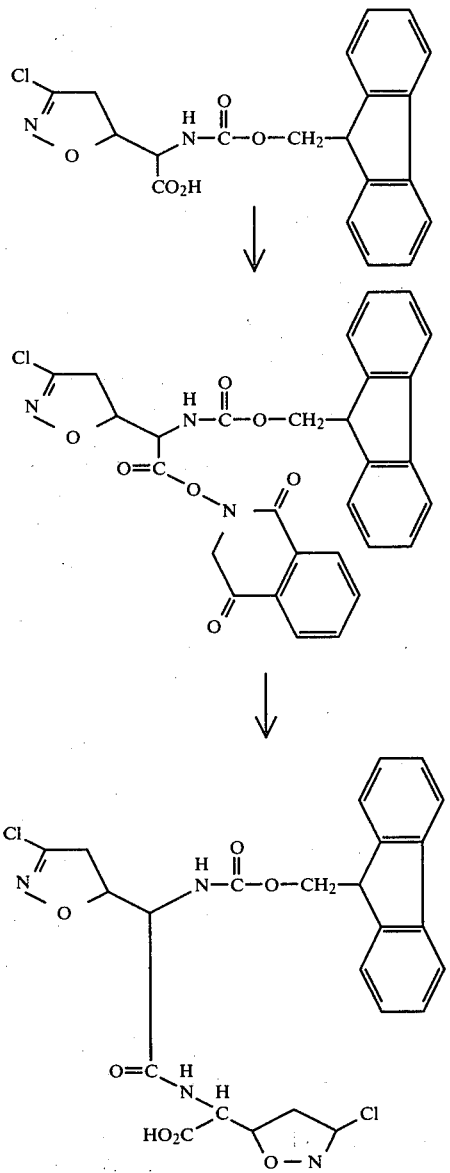

A solution of 500 mg. 3-chloro-α-[[(9H-fluoren-9-yl-methoxy)carbonyl]amino]-4,5-dihydro-5-isoxazoleacetic acid and 222 mg of n-hydroxyphthalimide in 10 ml dioxane is added to 270 mg of dicyclohexylcarbodiimide. The mixture is stirred for 45 minutes at room temperature. A suspension of 222 mg of 3-chloro-α-[[(9H-fluoren-9-ylmethoxy)carbonyl]amino]-4,5-dihydro-5-isoxazoleacetic acid in 2 ml of water is brought to pH 8.8 with 1 N sodium hydroxide and diluted with water dropwise until solution is effected; this solution is added to the above reaction mixture and stirred at room temperature for 1½ hours. The reaction is quenched with several drops of acetic acid, diluted to 150 ml with water, brought to pH 2.5 with aqueous hydrochloric acid, and extracted twice with 150 ml portions of ethyl acetate. Evaporation of these extracts affords 1.28 g of a crude mixture containing 3-chloro-α-[[(9H-fluoren-9-yl-methoxy)carbonyl]amino]-4,5-dihydro-5-isoxazoleacetic acid and 3-chloro-α-[[(3-chloro-4,5-dihydro-5-isoxazolyl)[[(9H-fluoren-9-ylmethoxy)carbonyl]amino]acetyl]amino]-4,5-dihydro-5-isoxazoleacetic acid. Chromatography on silica gel afforded 140 mg of recovered 3-chloro-α-[[(9H-fluoren-9-ylmethoxy)carbonyl]amino]-4,5-dihydro-5-isoxazoleacetic acid and 424 mg of 3-chloro-α-[[(3-chloro-4,5-dihydro-5-isoxazolyl)[[(9H)-fluoren-9-ylmethoxy)carbonyl]amino]acetyl]amino]-4,5-dihydro-5-isoxazoleacetic acid (61% yield at chromatographically homogeneous product).

EXAMPLE 1: Pure AT-125

A 2.56 g sample of 3-chloro-α-[[(1,1-dimethylethoxy)carbonyl]amino]-4,5-dihydro-5-isoxazoleacetic acid prepared as in Preparation 1 is dissolved in 25 ml of 5% anhydrous hydrogen chloride in glacial acetic acid. After 20 minutes at room temperature with sufficient agitation to insure complete dissolution of the gum, the resulting crystalline suspension is diluted to 250 ml with ethyl acetate. The essentially white crystals of 3-chloro-α-[[(1,1-dimethylethoxy)carbonyl]amino]-4,5-dihydro-5-isoxazoleacetic acid hydrochloride are collected, washed with ethyl acetate and dried affording 1.490 gm (87% overall yield). These crystals are dissolved in 100 ml of deionized water, adjusted to pH 5.6 with 1 N ammonium hydroxide and filtered through a coarse glass fritted funnel to remove lint. The filtrate is concentrated under reduced pressure to 80 ml and diluted with agitation to 640 ml with secondary butanol. The resulting white suspension is chilled overnight; the crystals are collected, washed with absolute methanol and dried affording 1.054 gm (74% overall) of analytically pure (αS,5S)-amino-3-chloro-4,5-dihydro-5-isoxazoleacetic acid. Concentrations of the mother liquor and methanol washes under reduced pressure to 80 ml affords additional crystalline material. After chilling the suspension several hours, the crystals are collected, washed thoroughly with methanol (to remove ammonium chloride) and dried affording an additional 115 mg (8% overall) of pure AT-125.

An alternate and more convenient method for obtaining the acid addition salt is to dissolve the 3-chloro-[[(1,1-dimethylethoxy)carbonyl]amino]-4,5-dihydro-5-isoxazoleacetic acid in glacial acetic acid (10 ml acid per gram of 3-chloro-α-[[(1,1-dimethylethoxy)carbonyl]amino]-4,5-dihydro-5-isoxazoleacetic acid derivative) followed by addition of concentrated hydrochloric acid (1.3 ml acid per gram of 3-chloro-α-[[(1,1-dimethylethoxy)carbonyl]amino]-4,5-dihydro-5-isoxazoleacetic acid derivative).

EXAMPLE 2: AT-125 from its phthalimido derivative

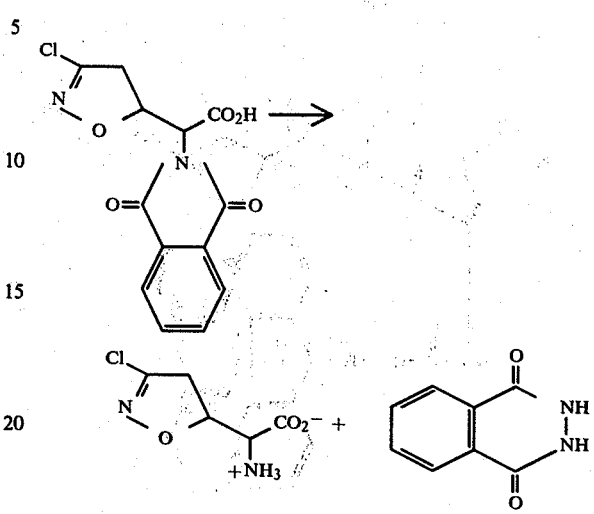

To a suspension of 172 mg (0.56 mmoles) of phthalyl-(2S,5S)-2-amino-3-chloro-4,5-dihydro-5-isoxazoleacetic acid prepared as in Preparation 2, in 3.3 ml of deionized water is added 56 μl (ca. 56 mg or 1.12 mmoles) of hydrazine hydrate. The resulting solution is kept at 50° for 6 hours. Solids present are collected, washed with 3 portions of water totalling 2 ml. and dried affording 21 mg of phthalazine dione, m.p. >310°. The filtrate 5.3 ml at pH 7 is diluted to 6.6 ml and treated with 20 μl of glacial acetic acid. This brings the pH to 5.3 and affords an additional 21 mg of phthalazine dione as an immediate precipitate which is removed by filtration and washed with water. The filtrate is concentrated to 4 ml under reduced pressure, diluted with 28 ml of 2-butanol, and chilled overnight. The crystalline product is then collected, washed with methanol, and dried to yield 70 mg (70%) of pure AT-125.

EXAMPLE 3: AT-125 from its p-nitro-benzyloxycarbonyl derivative

A sample of 3-chloro-4,5-dihydro-α-[[[(4-nitrophenyl)methoxy]carbonyl]amino]-5-isoxazoleacetic acid prepared as in Preparation 3 is dissolved in methanol and the solution stirred under an atmosphere of hydrogen at a temperature of about 0° C. to 30° C. for ½ to 8 hours. Pure AT-125 is separated from the mixture by aqueous extraction and crystallization from aqueous alcohol.

EXAMPLE 4: AT-125 from its fluorenyl derivative

The fluorenylmethoxycarbonyl group can be removed with anhydrous ammonia or aliphatic amines according to literature procedures (J. Org. Chem. 37:3404–3409, 1972).

I claim:

1. A compound having the formula

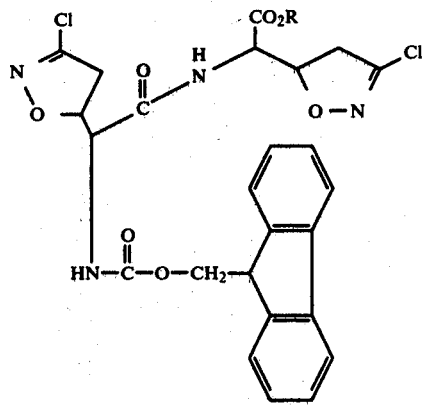

wherein R is selected from the group consisting of hydrogen and alkyl of from 1 to 8 carbon atoms, inclusive.

2. A compound according to claim 1 wherein $R_1$ is hydrogen so that the specific embodiment is 3-chloro-α-[[(3-chloro-4,5-dihydro-5-isoxazolyl)[[(9H-fluoren-9-ylmethoxy)carbonyl]amino]acetyl]amino]-4,5-dihydro-5-isoxazoleacetic acid.

3. A process for preparing a compound having the formula

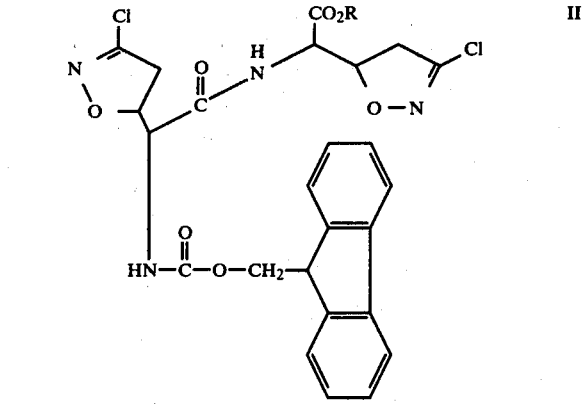

which comprises (a) reacting a compound having the formula

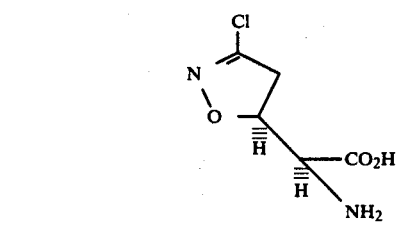

with a compound having the formula $$X-\overset{O}{\overset{\|}{C}}OCH_2-\text{(fluorenyl)}$$

and (b) recovering the compound of formula II from the reaction mixture formed in (a) wherein R is selected from the group consisting of hydrogen and alkyl of from 1 to 8 carbon atoms, inclusive and X is halogen, with the proviso that when R is alkyl of from 1 to 8 carbon atoms, inclusive the product of (b) must be subjected to esterification.

4. A process according to claim 3 wherein R is hydrogen and X is chlorine so that the compound prepared is 3-chloro-α-[[(3-chloro-4,5-dihydro-5-isoxazolyl)[[(9H-fluoren-9-ylmethoxy)carbonyl]amino]acetyl]amino]-4,5-dihydro-5-isoxazoleacetic acid.

* * * * *

UNITED STATES PATENT AND TRADEMARK OFFICE
CERTIFICATE OF CORRECTION

PATENT NO. : 4,225,720
DATED : September 30, 1980
INVENTOR(S) : David G. Martin

It is certified that error appears in the above—identified patent and that said Letters Patent is hereby corrected as shown below:

Column 2, line 55 (Formula I'): "    $CO_2$" should read: --    $CO_2H$ --.

Column 3, line 10: "1 to 3 carbon atoms" should read: -- 1 to 8 carbon atoms --.

Column 5, line 28: "ane Acid" should read: -- ane. Acid --.

Column 5, line 35: "in the art For example" should read: -- in the art. For example --.

Column 8, line 10 (first Formula): "$\underset{N=C-}{\overset{|}{CH}}$" should read: -- $\underset{N=C-}{\overset{|}{CN}}$ --.

Column 8, line 49: "0.1 gm, and 0.1" should read: -- 0.1 gm, and <0.1 --.

Column 8, line 51: "260 ml" should read: -- 250 ml --.

Column 9, line 39: "fractions Column" should read: -- fractions. Column --.

Column 10, line 45: "[[9H-" should read: -- [[9(H- --.

Signed and Sealed this

Seventh Day of December 1982

[SEAL]

Attest:

Attesting Officer

GERALD J. MOSSINGHOFF
Commissioner of Patents and Trademarks